(12) United States Patent
Harrison

(10) Patent No.: US 8,313,465 B2
(45) Date of Patent: Nov. 20, 2012

(54) INJECTION DEVICE

(75) Inventor: Nigel D. Harrison, Linton (GB)

(73) Assignee: Cilag GmbH International (CH)

( * ) Notice: Subject to any disclaimer, the term of this patent is extended or adjusted under 35 U.S.C. 154(b) by 285 days.

(21) Appl. No.: 11/579,564

(22) PCT Filed: May 27, 2005

(86) PCT No.: PCT/GB2005/002108
§ 371 (c)(1),
(2), (4) Date: Aug. 27, 2008

(87) PCT Pub. No.: WO2005/115507
PCT Pub. Date: Dec. 8, 2005

(65) Prior Publication Data
US 2009/0012471 A1    Jan. 8, 2009

(30) Foreign Application Priority Data
May 28, 2004 (GB) .................................. 0412053.1

(51) Int. Cl.
*A61M 5/20* (2006.01)
(52) U.S. Cl. ........................................................ 604/136
(58) Field of Classification Search .................. 604/187, 604/218, 157, 134–137
See application file for complete search history.

(56) References Cited

U.S. PATENT DOCUMENTS

| | | | |
|---|---|---|---|
| 1,845,036 A | 2/1932 | Busher | |
| 2,019,382 A | 10/1935 | Aronson | |
| 2,531,267 A | 11/1950 | Harisch | |
| 2,764,977 A | 10/1956 | Ferguson | |
| 2,828,742 A | 4/1958 | Ashkenaz | |
| 3,329,146 A | 7/1967 | Waldman | |
| 3,543,603 A | 12/1970 | Gley | |
| 3,656,472 A | 4/1972 | Moura | |
| 3,702,608 A | 11/1972 | Tibbs | |
| 3,742,948 A | 7/1973 | Post et al. | |
| 3,797,488 A | 3/1974 | Hurschman et al. | |
| 3,797,489 A | 3/1974 | Sarnoff | |

(Continued)

FOREIGN PATENT DOCUMENTS

CH          518102 A       1/1972

(Continued)

OTHER PUBLICATIONS

International Search Report dated Sep. 5, 2005; International Application No. PCT/GB2005/002117.

(Continued)

*Primary Examiner* — Nicholas Lucchesi
*Assistant Examiner* — Weng Lee

(57) ABSTRACT

An injection device 110 is described having a housing 112 that receives a syringe 114 having a needle 118, wherein the syringe is supported in a syringe carrier 150. The syringe 114 and syringe carrier 150 are biased by a return spring 126 from an extended position in which the needle 118 extends from the housing 112 through an exit aperture 128 to a retracted position in which it does not. A drive spring 130 acts via a drive to advance the syringe 114 from its retracted position to its extended position and discharge its contents through the needle 118 and a return spring 126, brought into play when the drive has reached a nominal return position, restores the syringe 114 to its retracted position. The injection device is less prone to failure than prior art devices and is safer should failure occur.

11 Claims, 3 Drawing Sheets

U.S. PATENT DOCUMENTS

| | | |
|---|---|---|
| 3,880,163 A | 4/1975 | Ritterskamp |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,231,368 A | 11/1980 | Becker |
| 4,299,238 A | 11/1981 | Baidwan et al. |
| 4,378,015 A | 3/1983 | Wardlaw |
| 4,394,863 A | 7/1983 | Bartner |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,744,786 A | 5/1988 | Hooven et al. |
| 4,787,891 A | 11/1988 | Levin et al. |
| 4,874,383 A | 10/1989 | McNaughton |
| 4,929,232 A | 5/1990 | Sweeney et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,156,599 A | 10/1992 | Ranford et al. |
| 5,176,643 A | 1/1993 | Kramer et al. |
| 5,190,526 A | 3/1993 | Murray et al. |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,330,430 A | 7/1994 | Sullivan |
| 5,358,489 A | 10/1994 | Wyrick |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,514,097 A | 5/1996 | Knauer |
| 5,520,653 A | 5/1996 | Reilly et al. |
| 5,540,660 A | 7/1996 | Jenson et al. |
| 5,540,709 A | 7/1996 | Ramel et al. |
| 5,567,160 A | 10/1996 | Massino |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,609,577 A | 3/1997 | Haber et al. |
| 5,609,584 A | 3/1997 | Gettig et al. |
| 5,637,094 A | 6/1997 | Stewart, Jr. et al. |
| 5,645,536 A | 7/1997 | Whisson |
| 5,647,845 A | 7/1997 | Haber et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,843,036 A | 12/1998 | Olive et al. |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,159,181 A | 12/2000 | Crossman et al. |
| 6,162,199 A | 12/2000 | Geringer |
| 6,171,276 B1 | 1/2001 | Markus et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,293,925 B1 * | 9/2001 | Safabash et al. ............... 604/136 |
| 6,371,939 B2 * | 4/2002 | Bergens et al. ............... 604/156 |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 * | 9/2002 | Weber ............................ 604/131 |
| 6,454,746 B1 | 9/2002 | Bydion et al. |
| 6,461,333 B1 | 10/2002 | Frezza |
| 6,517,517 B1 | 2/2003 | Farrugia et al. |
| 6,537,252 B1 * | 3/2003 | Hansen .......................... 604/157 |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,767,336 B1 | 7/2004 | Kaplan |

| Patent Number | Date | Name |
|---|---|---|
| 6,770,056 B2 | 8/2004 | Price et al. |
| 6,776,777 B2 | 8/2004 | Barrelle |
| 6,783,509 B1 | 8/2004 | Landau et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,634 B2 * | 8/2006 | Gilbert .......... 604/150 |
| 7,118,553 B2 | 10/2006 | Scherer |
| 7,156,823 B2 | 1/2007 | Landau et al. |
| 7,744,561 B2 | 6/2010 | Stamp |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0015134 A1 | 1/2004 | Lavi et al. |
| 2004/0019326 A1 | 1/2004 | Gilbert et al. |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0101919 A1 | 5/2005 | Brunnberg |
| 2005/0124940 A1 | 6/2005 | Martin et al. |
| 2005/0125019 A1 | 6/2005 | Kudrna et al. |
| 2005/0137523 A1 | 6/2005 | Wyatt et al. |
| 2005/0203466 A1 | 9/2005 | Hommann et al. |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184137 A1 | 8/2006 | Reynolds |
| 2006/0224124 A1 | 10/2006 | Scherer |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0078382 A1 | 4/2007 | Hommann et al. |
| 2007/0142787 A1 | 6/2007 | Scherer |
| 2008/0312606 A1 | 12/2008 | Harrison et al. |
| 2009/0054849 A1 | 2/2009 | Burnell et al. |
| 2009/0088688 A1 | 4/2009 | Timothy et al. |
| 2010/0016793 A1 | 1/2010 | Jennings et al. |

FOREIGN PATENT DOCUMENTS

| | | |
|---|---|---|
| CN | 2059579 U | 7/1990 |
| CN | 1190599 A | 8/1998 |
| CN | 1541121 A | 10/2004 |
| CN | 1550240 A | 12/2004 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 | 12/2004 |
| EP | 1364667 B1 | 4/2005 |
| EP | 1208858 B1 | 6/2006 |

| | | | | | | |
|---|---|---|---|---|---|---|
| EP | 1755710 | A1 | 2/2007 | WO | WO 93/02186 A1 | 2/1993 |
| EP | 1586341 | B1 | 1/2008 | WO | WO 93/21986 A2 | 11/1993 |
| EP | 1932558 | A1 | 6/2008 | WO | WO 93/23098 | 11/1993 |
| EP | 2023980 | A1 | 2/2009 | WO | WO 94/04207 | 3/1994 |
| EP | 2129414 | A1 | 12/2009 | WO | WO 94/07554 A1 | 4/1994 |
| EP | 1755706 | B1 | 3/2010 | WO | WO 94/11041 | 5/1994 |
| EP | 1928523 | B1 | 7/2010 | WO | WO 94/13342 A1 | 6/1994 |
| EP | 1518575 | B1 | 11/2010 | WO | WO 94/21316 A1 | 9/1994 |
| FR | 1014881 | A | 8/1952 | WO | WO 94/22511 A1 | 10/1994 |
| FR | 1169935 | A | 1/1959 | WO | WO 95/04562 A1 | 2/1995 |
| FR | 1538565 | A | 9/1968 | WO | WO 95/29720 | 11/1995 |
| FR | 2506161 | A1 | 11/1982 | WO | WO 95/31235 A1 | 11/1995 |
| FR | 2629706 | A | 10/1989 | WO | WO 95/35126 | 11/1995 |
| FR | 2654938 | A1 | 5/1991 | WO | WO 95/35126 A1 | 12/1995 |
| FR | 2665079 | A1 | 1/1992 | WO | WO 96/30065 A1 | 10/1996 |
| FR | 2717086 | A1 | 9/1995 | WO | WO 97/10865 A1 | 3/1997 |
| FR | 2741810 | A1 | 6/1997 | WO | WO 97/13538 | 4/1997 |
| FR | 2861310 | A1 | 4/2005 | WO | WO 97/48430 A1 | 12/1997 |
| GB | 143084 | | 5/1920 | WO | WO 98/11927 A1 | 3/1998 |
| GB | 0412054 | | 6/1934 | WO | WO 99/03529 A2 | 1/1999 |
| GB | 728248 | | 4/1955 | WO | WO 99/10030 A1 | 3/1999 |
| GB | 909898 | | 11/1962 | WO | WO 99/22789 | 5/1999 |
| GB | 1263355 | | 2/1972 | WO | WO 99/37343 A | 7/1999 |
| GB | 1311937 | A | 3/1973 | WO | WO 99/53979 A1 | 10/1999 |
| GB | 1514725 | | 6/1978 | WO | WO 99/59658 | 11/1999 |
| GB | 2338033 | A | 12/1999 | WO | WO 00/06227 A1 | 2/2000 |
| GB | 2388033 | A | 11/2003 | WO | WO 00/07539 A1 | 2/2000 |
| GB | 2396298 | A | 6/2004 | WO | WO 00/13723 A2 | 3/2000 |
| GB | 2396816 | A | 7/2004 | WO | WO 00/24441 A1 | 5/2000 |
| GB | 2397767 | A | 8/2004 | WO | WO 00/35516 | 6/2000 |
| GB | 2414398 | A | 11/2005 | WO | WO 00/50107 A1 | 8/2000 |
| GB | 2414399 | A | 11/2005 | WO | WO 00/64515 | 11/2000 |
| GB | 2414400 | A | 11/2005 | WO | WO 00/69488 A2 | 11/2000 |
| GB | 2414401 | A | 11/2005 | WO | WO 01/05456 A1 | 1/2001 |
| GB | 2414402 | A | 11/2005 | WO | WO 01/49347 A1 | 7/2001 |
| GB | 2414403 | A | 11/2005 | WO | WO 01/76666 A1 | 10/2001 |
| GB | 2424835 | A | 10/2006 | WO | WO 01/77384 A2 | 10/2001 |
| GB | 2424836 | A | 10/2006 | WO | WO 01/87384 A1 | 11/2001 |
| GB | 2424838 | A | 10/2006 | WO | WO 02/11799 A | 2/2002 |
| GB | 2433035 | A | 6/2007 | WO | WO 02/47746 A1 | 6/2002 |
| GB | 2437922 | A | 11/2007 | WO | WO 02/056947 A1 | 7/2002 |
| GB | 2438591 | A | 12/2007 | WO | WO 03/013632 A2 | 2/2003 |
| GB | 2446778 | A | 8/2008 | WO | WO 03/015853 A1 | 2/2003 |
| JP | 59-115053 | A | 7/1984 | WO | WO 03/039633 | 5/2003 |
| JP | 2-185261 | A | 7/1990 | WO | WO 03/041768 A | 5/2003 |
| JP | 2-502971 | T | 9/1990 | WO | WO 03/047663 A2 | 6/2003 |
| JP | 11-501549 | T | 2/1992 | WO | WO 03/051434 | 6/2003 |
| JP | 5-161712 | A | 6/1993 | WO | WO 03/066141 A1 | 8/2003 |
| JP | 6-209996 | A | 8/1994 | WO | WO 03/092771 | 11/2003 |
| JP | 6-508773 | T | 10/1994 | WO | WO 03/097133 | 11/2003 |
| JP | 6-327770 | A | 11/1994 | WO | WO 03/099358 A2 | 12/2003 |
| JP | 7-222799 | A | 8/1995 | WO | WO 2004/007554 A1 | 1/2004 |
| JP | 8-502180 | T | 3/1996 | WO | WO 2004/011065 A | 2/2004 |
| JP | 8-504354 | T | 5/1996 | WO | WO 2004/030732 A2 | 4/2004 |
| JP | 9-225029 | A | 9/1997 | WO | WO 2004/035117 | 4/2004 |
| JP | 10-504474 | T | 5/1998 | WO | WO 2004/047890 A1 | 6/2004 |
| JP | 10-507935 | A | 8/1998 | WO | WO 2004/047891 | 6/2004 |
| JP | 11-503637 | T | 3/1999 | WO | WO 2004/047892 A | 6/2004 |
| JP | 11-504536 | T | 4/1999 | WO | WO 2004/054644 A1 | 7/2004 |
| JP | 11-164887 | T | 6/1999 | WO | WO 2004/054645 A3 | 7/2004 |
| JP | 11-512332 | T | 10/1999 | WO | WO 2004/087242 A1 | 10/2004 |
| JP | 2000-510021 | T | 8/2000 | WO | WO 2004/108194 A | 12/2004 |
| JP | 2002-500933 | T | 1/2002 | WO | WO 2005/009515 A1 | 2/2005 |
| JP | 2002-095749 | A | 4/2002 | WO | WO 2005/023341 A1 | 3/2005 |
| JP | 2002-513547 | T | 5/2002 | WO | WO 2005/025636 A2 | 3/2005 |
| JP | 2002-526175 | A | 8/2002 | WO | WO 2005/030301 A1 | 4/2005 |
| JP | 2002-528182 | T | 9/2002 | WO | WO 2005/035028 A1 | 4/2005 |
| JP | 2002-532161 | T | 10/2002 | WO | WO 2005/044345 A | 5/2005 |
| JP | 2003-511105 | T | 3/2003 | WO | WO 2005/044347 A1 | 5/2005 |
| JP | 2003-532500 | T | 11/2003 | WO | WO 2005/058396 A1 | 6/2005 |
| JP | 2003-533288 | A | 11/2003 | WO | WO 2005/070481 A1 | 8/2005 |
| JP | 2004-533282 | T | 11/2004 | WO | WO 2005/082438 | 9/2005 |
| JP | 2004-33737 | A | 8/2005 | WO | WO 2005/097238 | 10/2005 |
| NZ | 573171 | A | 11/2010 | WO | WO 2005/115507 A1 | 12/2005 |
| NZ | 573350 | A | 12/2010 | WO | WO 2005/115508 A1 | 12/2005 |
| WO | WO 88/08725 | | 11/1988 | WO | WO 2005/115509 A1 | 12/2005 |
| WO | WO 88/10129 | | 12/1988 | WO | WO 2005/115510 A1 | 12/2005 |
| WO | WO 98/10129 | A1 | 12/1988 | WO | WO 2005/115512 A1 | 12/2005 |
| WO | WO 92/19296 | A | 11/1992 | WO | WO 2005/115513 A1 | 12/2005 |

| | | |
|---|---|---|
| WO | WO 2005/115514 A1 | 12/2005 |
| WO | WO 2005/120607 A2 | 12/2005 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2 (CCS5050GBNP).
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.

* cited by examiner

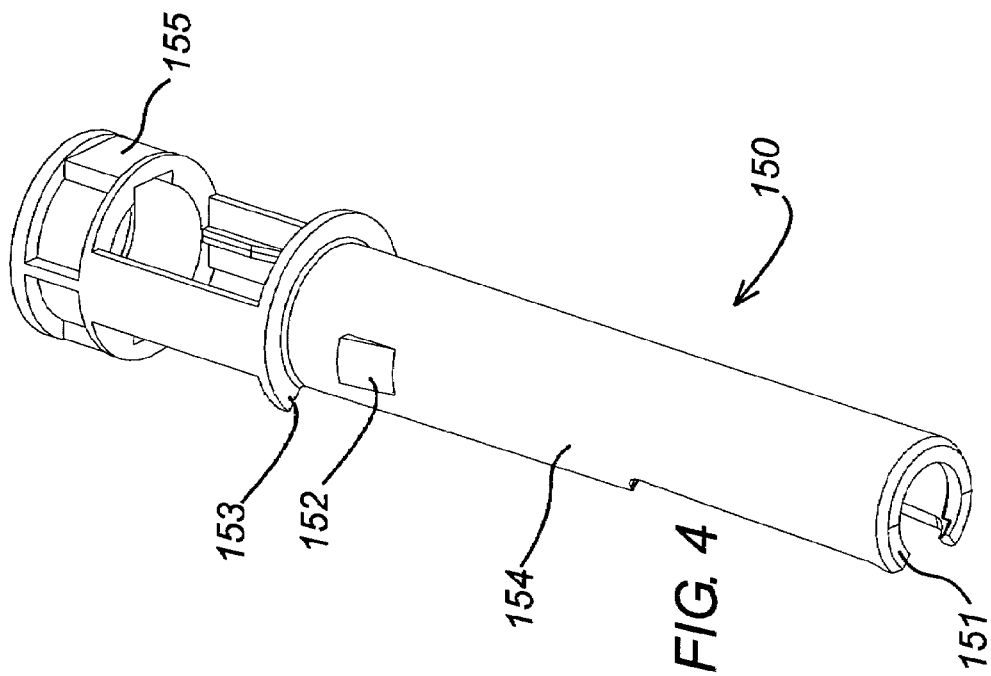
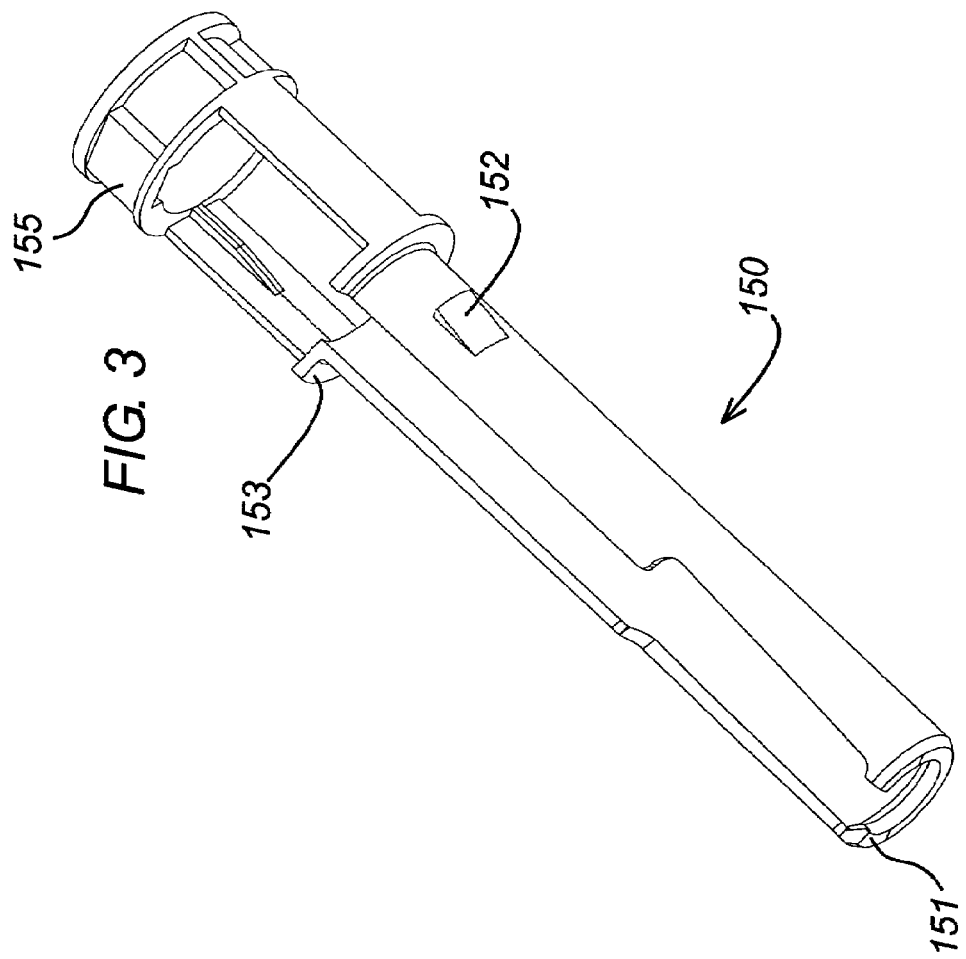

INJECTION DEVICE

BACKGROUND TECHNOLOGY

The present invention relates to an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Often, such injection devices are required to work with glass pre-filled syringes that were originally designed for manual use. Such glass syringes have a flange at their base to allow a user to grip the syringe. The substantial force produced by the drive spring is applied to the piston of the syringe. This force is transferred to the housing and return spring, via the flange. The flanges are not precision molded and consequently have low manufacturing tolerances. They are not sufficiently flat or consistent to be used as a satisfactory support means for the syringe through which the force of the drive spring is transferred to the housing and return spring.

In practice, these flanges have been seen to fail when the drive spring is employed and the force produced by the drive spring is applied, via the piston of the syringe, to the flange. In particular, these flanges have been seen to break off from the syringe, resulting in the syringe body being propelled from the front of the injection device, and the whole needle being inserted into the user's body. Consequently, when the injection device is taken away from the user's body, a full, broken syringe is left dangling from the user's body. This is clearly dangerous because the user is left with a broken syringe, and consequently broken glass, dangling from their body. The user is also left without having had their correct dose of drug. Such a syringe failure is also, of course, unpleasant for any user, particularly those that are squeamish.

SUMMARY OF THE INVENTION

The injection devices of the present invention are designed to deal with these problems.

An injection device according to the present invention comprises:
- a housing adapted to receive a syringe having a relatively wide reservoir portion and a relatively narrow discharge nozzle, so that the syringe is movable between a retracted position in which the discharge nozzle is contained within the housing and an extended position in which the discharge nozzle extends from the housing through an exit aperture;
- a drive that acts upon the syringe to advance it from its retracted position to its extended position and discharge its contents through the discharge nozzle; and
- a syringe carrier for carrying the syringe as it is advanced and restraining its advancement beyond its extended position, wherein the syringe carrier is adapted to support the syringe between the reservoir portion and the discharge nozzle.

The syringe carrier may provide an interface between the syringe and the housing.

The syringe carrier may comprise an annular collet having an internal diameter that is smaller than an outer diameter of the reservoir portion of the syringe. The annular collet may be adapted to support the syringe between the reservoir portion and the discharge nozzle. The annular collet may be a split annular collet.

The syringe carrier may further comprise a sheath for surrounding the reservoir portion of the syringe, having a first internal diameter along its length, and further having a first end with a second internal diameter which is smaller than the first internal diameter so that the first end of the sheath is adapted to support the syringe between the reservoir portion and the discharge nozzle. The sheath may be split.

By supporting the syringe close to its first end with the syringe carrier, any force applied to the housing by the drive spring is transferred to the housing via the first end of the syringe. No force is transferred via any flange of the syringe. The first end of the syringe has been found to be stronger than the flange of the syringe, and to be less prone to failure. In particular, tests have been carried out in which impact loads have been applied to the piston of a filled syringe. In tests where the syringe was supported in a rubber buffer under the flange, a mass of 1.6 kg dropped from 50 mm would almost always result in a broken syringe. In tests where the syringe was supported on a conical collet under the end of the syringe nearest to the discharge nozzle, the syringes would almost always withstand the same mass being dropped from 75 mm. Generally, when the syringe was supported on a conical collet under the end of the syringe nearest to the discharge nozzle, multiple impacts were required for failure.

By surrounding the syringe with the syringe carrier close to its first end, if the syringe does fail, it will not be propelled from the end of the device because it will not be able to fit through the part of the syringe carrier which has a reduced diameter.

By providing a sheath that is split, the syringe can be inserted into the syringe carrier through the split of the sheath. Generally, syringes are provided with a boot which covers the discharge nozzle. The boot is generally of larger diameter than the body of the syringe. By providing a split sheath, the syringe can be inserted into the sheath, without having to remove the boot from the syringe. This is advantageous because it is a requirement that the discharge nozzle of the syringe remains sterile for as long as possible before the injection device is used.

The injection device may further comprise means for biasing the syringe from its extended position to its retracted position and a support for carrying the means for biasing the syringe. The means for biasing may comprise a return spring. The syringe carrier may further comprise means for bearing against the support. The means for bearing may comprise a portion having an external diameter which is greater than the external diameter of any portion of the syringe carrier situated between the means for bearing and the discharge nozzle.

The syringe carrier may further comprise a ramped surface, and the support may further comprise a corresponding locking surface, wherein the ramped surface is adapted to communicate with the locking surface so as to lock the syringe carrier relative to the support.

The injection device may further comprise a drive element and the syringe carrier may further comprise an annular portion which is adapted to act as part of a release mechanism and couple with the drive element in order to disconnect the drive element from the drive and allow the return spring to move the syringe from its extended position to its retracted position.

BRIEF DESCRIPTION OF THE DRAWINGS

The invention will now be described by way of example with reference to the accompanying drawings, in which:

FIG. 3 shows a perspective view of a syringe carrier for use in the present invention from a first direction;

FIG. 4 shows a perspective view of the syringe carrier of FIG. 3 from a second direction.

DETAILED DESCRIPTION

Figure 1:
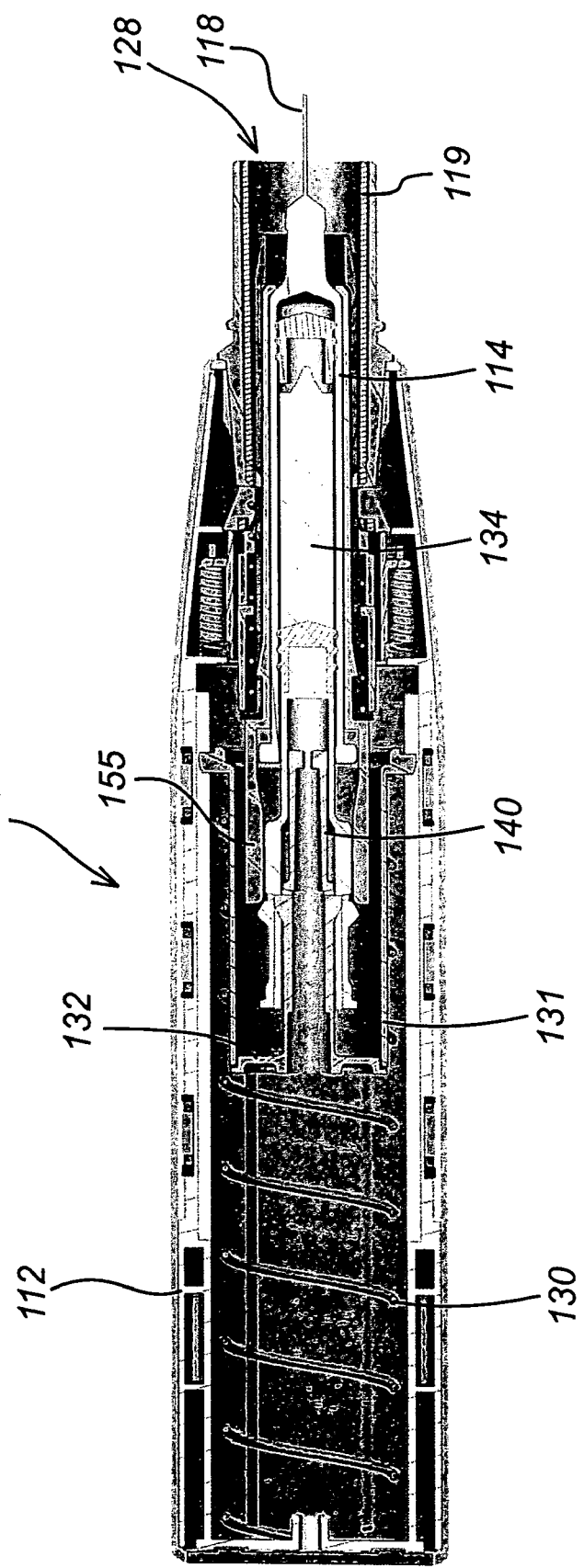
FIG. 1 shows a cross-sectional view of an injection device according to the present invention.
Figure 2:
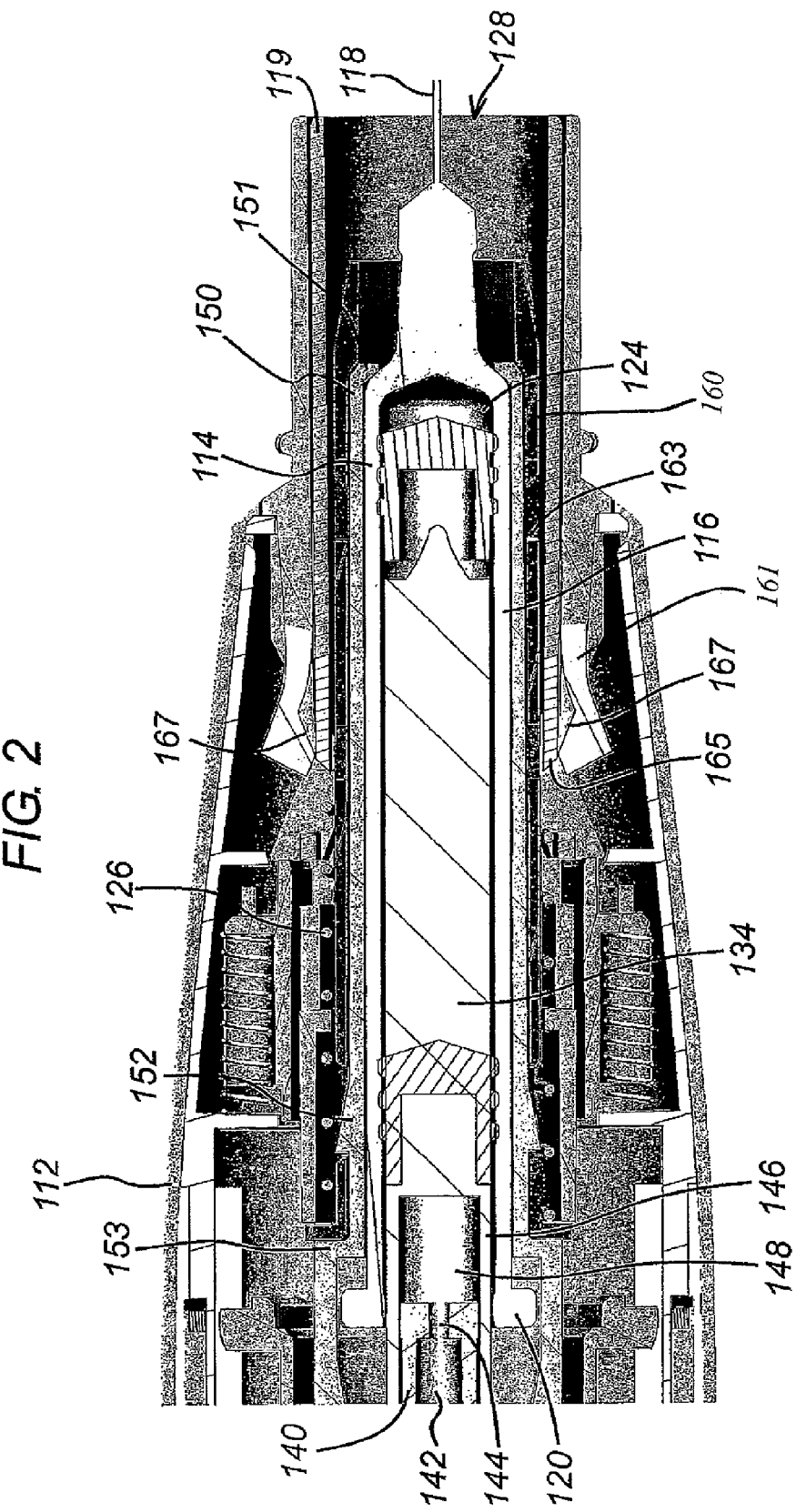
FIG. 2 shows an enlarged part of the injection device shown in FIG. 1.

FIGS. 1 and 2 show an injection device 110, having an injection device housing 112. The end of the housing 112 has an exit aperture 128, through which the end of a sleeve 119 can emerge.

The housing 112 contains a hypodermic syringe 114 of conventional type, including a syringe body 116 defining a reservoir and terminating at one end in a hypodermic needle 118 and at the other in a flange 120. The syringe body 116 is of substantially constant diameter along the length of the reservoir, and is of significantly smaller diameter close to the end of the syringe which terminates in the hypodermic needle. A drive element 134 acts through the bung of the syringe to discharge the contents of the syringe 114 through the needle 118. This drive element 134 constrains a drug 124 to be administered within the reservoir defined by syringe body 116. Whilst the syringe illustrated is of hypodermic type, this need not necessarily be so. Transcutaneous or ballistic dermal and subcutaneous syringes may also be used with the injection device of the present invention.

As illustrated, the syringe is housed within a syringe carrier 150. The syringe carrier is best seen in FIGS. 3 and 4. The syringe carrier 150 has a first end 151 which has a reduced diameter. The first end 151 of the syringe carrier supports the end of the syringe 114 nearest to the hypodermic needle. Close to the other end of the syringe carrier 150, are provided a pair of ramped projections 152. The pair of ramped projections 152 communicate with a corresponding pair of locking apertures on a return spring support 160 so that the syringe carrier 150 cannot move relative to the return spring support 160. The syringe carrier 150 also comprises a bearing surface 153 close to its second end, against which a corresponding bearing surface of the return spring support 160 is biased by a return spring 126. The return spring 126, via the return spring support 160 and the syringe carrier 150 biases the syringe 114 from an extended position in which the needle 118 extends from the aperture 128 in the housing 112 to a retracted position in which the needle 118 is contained within the housing 112.

The syringe carrier 150 comprises a sheath 154 which is split along its length so that the syringe 114 can be clipped into the syringe carrier 150. The syringe 114 is provided with a boot (not shown). By providing a syringe carrier 150 in the form of a split sheath 154, the syringe 114 can be inserted into the syringe carrier 150 and in turn into the injection device 110 without having to remove the boot from the syringe 114. Furthermore, if the syringe were to fail or break, the sheath 154, which substantially surrounds the syringe 114 along its length, would contain the broken pieces of syringe and reduce the likelihood of them from escaping from the injection device.

The housing is further provided with a resilient latch member 161 that is biased into a position in which it engages a locking surface 163 on the return spring support 160. Before engaging the locking surface 163, the latch member 161 also extends through a latch opening 165 in the sleeve 119. The latch member 161 includes a ramped surface 167 against which an edge of the latch opening 165 acts in the manner of a cam acting on a cam follower.

The housing also includes an actuator, and a drive which here takes the form of a compression drive spring 130. Drive from the drive spring 130 is transmitted via a multi-component drive to the piston of the syringe 114 to advance the syringe from its retracted position to its extended position and discharge its contents through the needle 118. The drive accomplishes this task by acting directly on the drug 124 and the syringe 114. Static friction between the drive element 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a first drive element 132. This in turn transmits drive to the drive element 134 already mentioned.

The drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 define a fluid reservoir 148, within which a damping fluid is contained.

A trigger (not shown) is provided on the housing 112 remote from the exit aperture 128. The trigger, when operated, serves to decouple the drive sleeve 131 from the housing 112, allowing it to move relative to the housing 112 under the influence of the drive spring 130. The operation of the device is then as follows.

Initially, the return spring support 160, and consequently the syringe carrier 150 and syringe 114, are prevented from movement by the resilient latch member 161. By moving the sleeve 119 in a direction into the housing 112, the edge of the latch opening 165 is brought into contact with the ramped surface 167 of the latch member 161, causing the latch member 161 to move outwards and thus to disengage from the return spring support 160. Once the latch member 161 has disengaged from the locking surface 163, the syringe is free to move.

The actuator is then depressed and the drive spring 130 is released. The drive spring 130 moves the drive sleeve 131, the drive sleeve 131 moves the first drive element 132 and the first drive element 132 moves the second drive element 134. The second drive element 134 moves and, by virtue of static friction and hydrostatic forces acting through the drug 124 to be administered, moves the syringe body 114 against the action of the return spring 126. The syringe body 114 moves the syringe carrier 150, which in turn moves the return spring support 160 and compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic and hydrodynamic forces now acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, flexible latch arms linking the first and second drive elements 132, 134 reach a constriction within the housing 112 formed by an annular portion 155 at the end of the syringe carrier which is nearest to the flange 120 of the syringe 114. The constriction moves the flexible latch arms to a position so that they no longer couple the first drive element 132 to the second drive element 134. Once this happens, the first drive element 132 acts no longer on the second drive element 134, allowing the first drive element 132 to move relative to the second drive element 134.

Because the damping fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, damping fluid is forced through the vent 144 into the collection chamber 142. Thus, once the flexible latch arms have been released, some of the force exerted by the drive spring 130 does work on the damping fluid, causing it to flow though the constriction formed by the vent 144; the remainder acts hydrostatically through the fluid and through friction between the first and second drive elements 132, 134, thence via the second drive element 134. Consequently, the second drive element 134 continues to move within the syringe body 116 and the drug 124 continues to be discharged. Losses associated with the flow of the damping fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow though the vent 144, allowing the first drive element 132 to continue its movement.

Before the reservoir 148 of fluid is exhausted, flexible latch arms linking the drive sleeve 131 with the first drive element 132 reach another constriction within the housing 112. The constriction moves the flexible latch arms so that they no longer couple the drive sleeve 131 to the first drive element 132. Once this happens, the drive sleeve 131 acts no longer on the first drive element 132, allowing them to move relative each other. At this point, the forces developed by the drive spring 130 are no longer being transmitted to the syringe 114. The only force acting on the syringe will be the return force from the return spring 126 which acts on the end of the syringe 114 nearest to the needle 118 via the return spring support 160 and the syringe carrier 150. Consequently, the syringe is returned to its retracted position and the injection cycle is complete.

The invention claimed is:

1. An injection device comprising:
   a housing adapted to receive a syringe having a relatively wide reservoir portion and a relatively narrow discharge nozzle, so that the syringe is movable between a retracted position in which the discharge nozzle is contained within the housing and an extended position in which the discharge nozzle extends from the housing through an exit aperture;
   a drive element that acts upon the syringe;
   a drive that acts upon the drive element to advance the syringe from its retracted position to its extended position and discharge its contents through the discharge nozzle;
      a syringe carrier movable within the housing for carrying the syringe as it is advanced and restraining its advancement beyond its extended position,
      wherein the syringe carrier is adapted to support the syringe between the reservoir portion and the discharge nozzle,
      wherein the syringe carrier comprises an annular portion which is adapted to act as part of a release mechanism and couple with the drive element in order to disconnect the drive element from the drive.

2. An injection device according to claim 1, wherein the syringe carrier provides an interface between the syringe and the housing.

3. An injection device according to claim 1 wherein the syringe carrier comprises an annular collet having an internal diameter that is smaller than an outer diameter of the reservoir portion of the syringe, wherein the annular collet is adapted to support the syringe between the reservoir portion and the discharge nozzle.

4. An injection device according to claim 3 wherein the annular collet is a split annular collet.

5. An injection device according to claim 1 in which the syringe carrier comprises a sheath for surrounding the reservoir portion of the syringe, wherein the sheath has a first internal diameter along its length, and a first end with a second internal diameter which is smaller than the first internal diameter so that the first end of the sheath is adapted to support the syringe between the reservoir portion and the discharge nozzle.

6. An injection device according to claim 5 in which the sheath is split along its length.

7. An injection device according to claim 1 further comprising means for biasing the syringe from its extended position to its refracted position.

8. An injection device according to claim 7, further comprising a support for carrying the means for biasing the syringe.

9. An injection device according to claim 8, wherein the syringe carrier further comprises means for bearing against the support.

10. An injection device according to claim 9 in which the means for bearing comprises a portion having an external diameter which is greater than the external diameter of any portion of the syringe carrier situated between the means for bearing and the discharge nozzle.

11. An injection device according to claim 8 in which the syringe carrier further comprises a ramped surface, and the support further comprises a corresponding locking surface, wherein the ramped surface is adapted to communicate with the locking surface so as to lock the syringe carrier relative to the support.

* * * * *